United States Patent [19]

Cramer et al.

[11] Patent Number: 5,069,552
[45] Date of Patent: Dec. 3, 1991

[54] SENSOR-HOLDING DEVICE

[75] Inventors: Gregory D. Cramer; Roger A. Dupre, both of Seaford, Del.; George H. Hitchcock, Charlotte, N.C.

[73] Assignee: E. I. du Pont de Nemours and Company, Wilmington, Del.

[21] Appl. No.: 444,778

[22] Filed: Dec. 1, 1989

[51] Int. Cl.⁵ .......................................... G01N 21/85
[52] U.S. Cl. ................................. 356/440; 356/436
[58] Field of Search .................. 356/440, 436, 246, 73; 250/345

[56] References Cited

U.S. PATENT DOCUMENTS

| | | | |
|---|---|---|---|
| 3,020,795 | 2/1962 | McKinney et al. | 88/14 |
| 3,584,964 | 6/1971 | Nejame Jr. | 356/244 |
| 3,728,032 | 4/1973 | Noll | 356/246 |
| 3,810,695 | 5/1974 | Shea | 356/73 |
| 3,886,364 | 5/1975 | Walker et al. | 250/343 |
| 3,936,196 | 2/1976 | Wickersheim | 356/246 |
| 3,940,618 | 2/1976 | Donguy | 250/304 |
| 4,098,119 | 7/1978 | Coats | 73/323 |
| 4,165,179 | 8/1979 | Sato | 356/246 |
| 4,281,935 | 4/1981 | Cramer et al. | 366/174 |
| 4,319,138 | 3/1982 | Sweet | 250/576 |
| 4,400,097 | 8/1983 | Koschnitzke et al. | 374/121 |
| 4,408,878 | 10/1983 | Fischbach | 356/43 |
| 4,492,868 | 1/1985 | Jelvestam et al. | 250/345 |
| 4,516,864 | 5/1985 | Kim et al. | 374/130 |
| 4,529,306 | 7/1985 | Kilham et al. | 356/237 |
| 4,872,753 | 10/1989 | Dangiel et al. | 356/246 |

Primary Examiner—Vincent P. McGraw
Assistant Examiner—LaCharles P. Keesee, II

[57] ABSTRACT

An apparatus for the analysis of a fluid flowing in a stream includes opposed hollow stems movable in a body member relative to each other. One stem contains a signalling source and the other contains a sensor for the signalling source.

5 Claims, 4 Drawing Sheets

SENSOR-HOLDING DEVICE

BACKGROUND O THE INVENTION

This invention relates to a sensor-holding device and, more particularly, to a sensor-holding device which permits removal of sensors used for on-line measurements of a fluid stream flowing in a pipe without interrupting fluid flow.

Existing on-line fluid rheological, physical property, and particulate-sensing devices are mounted flush with the pipe wall and tend to coat with fouling residue resulting in inaccurate measurements or premature failure of the sensor. Such an arrangement does not allow for on-line cleaning, maintenance, adjustment, or replacement of the sensor elements. It instead requires shutdown and flushing of the system in order to remove the sensor components for replacement or maintenance, which takes considerable time and reduces production output.

SUMMARY OF THE INVENTION

The present invention overcomes these problems by providing a sensor-holding device which allows for easy on-line maintenance or replacement of sensors without fluid stream shutdown. The device is useful for holding a wide variety of sensor types, including, but not limited to, light, ultrasonic, temperature and pressure sensors. In one embodiment, the device provides stems which may be advanced and retracted independently so as to allow for both the adjustment of the distance between sensor windows or ends and adjustment of the position of the sensors in the fluid stream. One or both stems may be hollow to hold a one or two component sensor, respectively. When the stems are in their fully advanced positions, intimate and leak-proof contact of the stems is provided between the two mating stem surfaces. This permits the sensor elements to be removed for maintenance and reinstalled with no interruption of the fluid stream.

DETAILED DESCRIPTION OF THE ILLUSTRATED EMBODIMENTS

Figure 1:
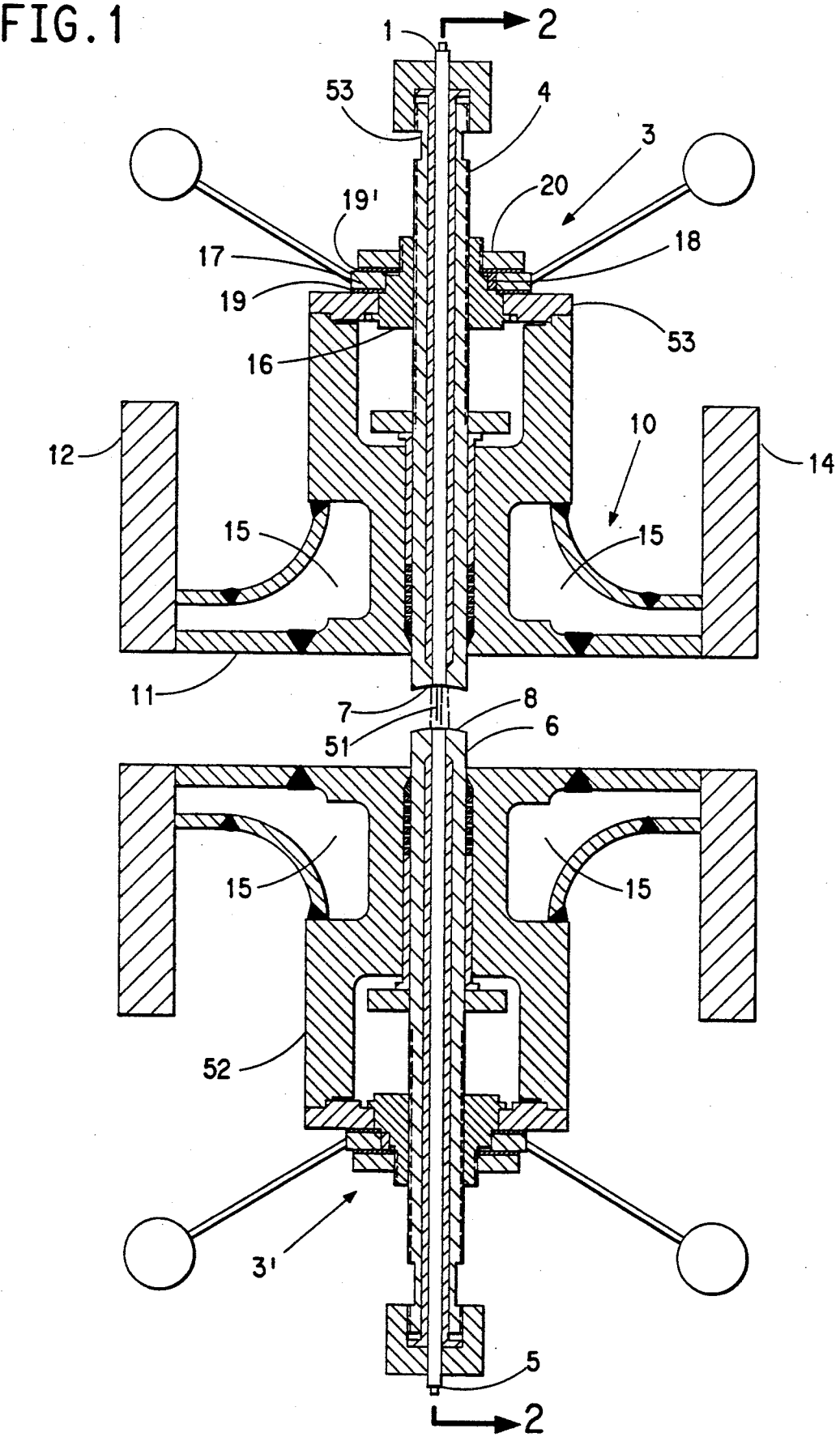
FIG. 1 is a cross-sectioned side elevation view illustrating an embodiment of the present invention in which both stems may be advanced and retracted without rotating, and may be advanced and retracted independently of each other, and in which sensor elements are contained in both stems of the device.
Figure 2:
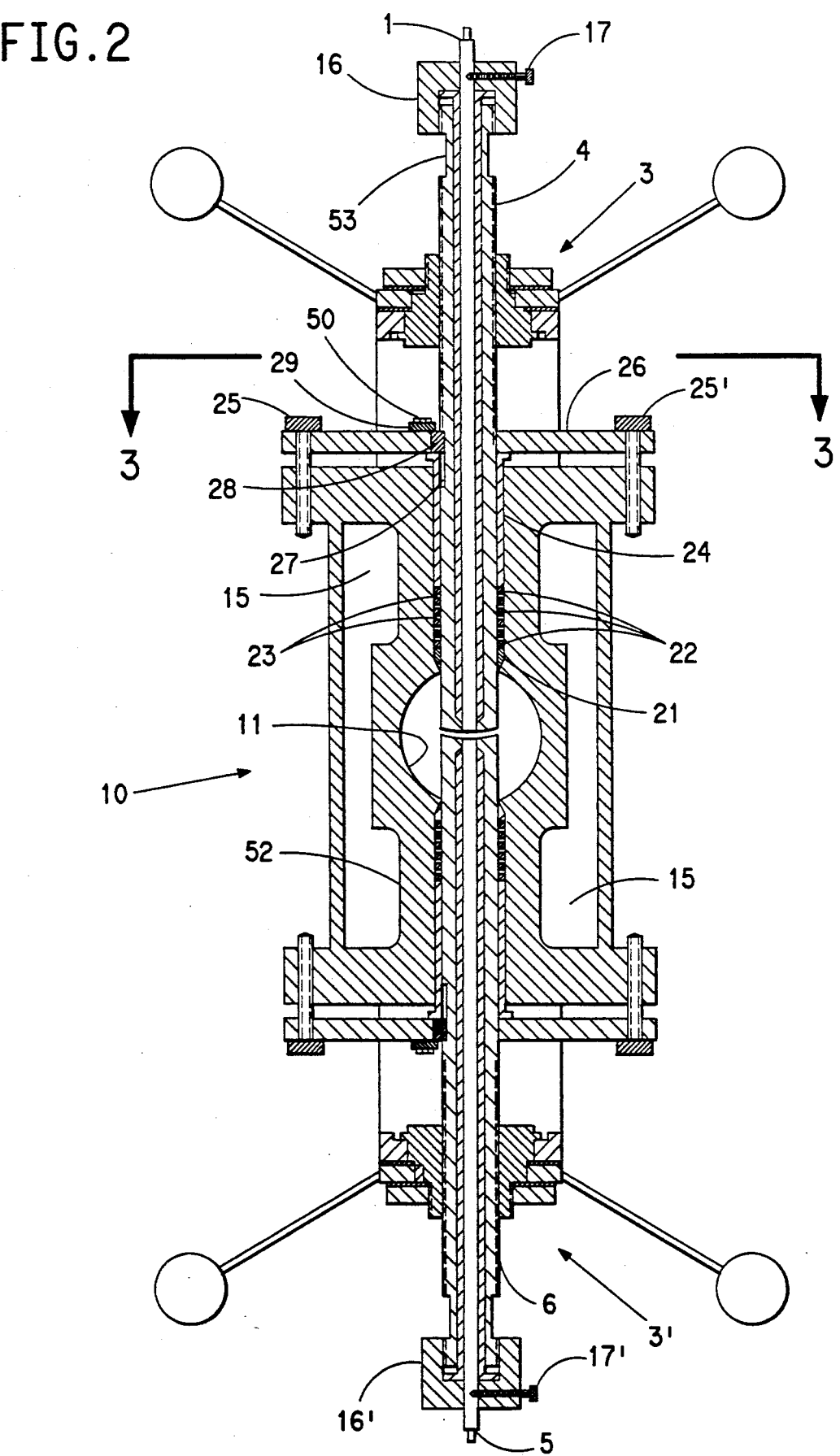
FIG. 2 is a cross-sectioned end elevation view of FIG. 1 taken along line 2—2.
Figure 3:
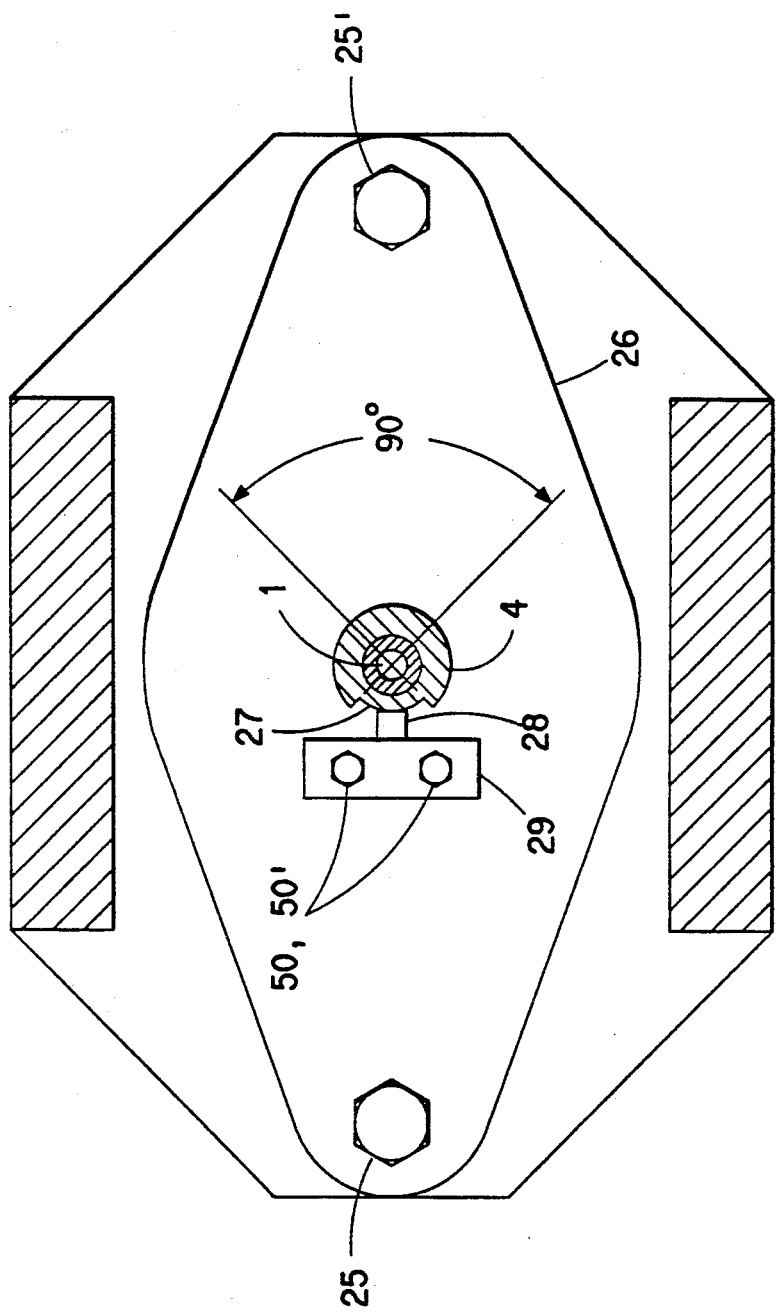
FIG. 3 is a plan view partially in section of FIG. 1 illustrating the rotational mechanism for rotating the stems.

Referring to FIGS. 1-3, the sensing apparatus includes a body 10 defining a fluid flow path 11 therethrough from an inlet end flange 12 to an outlet end flange 14 for connection to subsequent piping. The body may also be welded directly into an existing pipeline Non-rotating hollow stems 4 and 6 are advanced and retracted by means of stem operating mechanisms 3 and 3'. In the particular embodiment shown, 3 and 3' are rising stem mechanisms assembled from nut 16 which is keyed to handle 17 by key 18. Washers 19 and 19' are inserted between handle 17 and device body flange 53 and nut 20. Nut 20 is threaded onto 16 to secure the rising stem mechanism together. Rotation of handle 17 causes nut 16 to rotate which results in the upward or downward motion of stem 4 which is threaded into nut 16. Slot 27 machined into stem 4 restricts the travel distance of the stem by means of key 28. The key is captured by plate 29 secured by bolts 50 and 50' to plate 26. An identical arrangement is provided for stem 6. Use of a rising stem mechanism eliminates any problems with entanglement of wires or other connections to the sensor probes that might occur if the stem were required to rotate when advanced and retracted. However, a rotating stem could be effectively employed with a swivel coupling for the sensor lead wire or other means of instrument signal transmission.

The sensor components consist of observation and illumination probes 1 and 5 used for particle detection. An example of such a sensor is described in U.S. Pat. No. 4,529,306. The probes 1 and 5 are contained in the hollow stems 4 and 6, respectively They are held in place and maintained in a leak-tight condition by being either in a packing arrangement with or being threaded or gasketed into the stems 4 and 6. Probes 1 and 5 are further secured in the stems by means of caps 16 and 16' and lock screws 17 and 17'.

A packing arrangement is used to maintain stems 4 and 6 in a leaktight condition in device body 52. More particularly, the packing arrangement (FIGS. 1 and 2) is assembled from bushing 21, packing rings 22 separated by metal waters 23, and sleeve 24 which acts as a packing follower. This packing arrangement may be compressed to effect a leaktight seal by tightening screws 25 and 25' which are threaded through plate 26 which presses against sleeve 24 and device body 52. This packing arrangement prevents fluid from the pipeline from leaking between the stems and the body of the device. The sensors 1 and 5 are recessed slightly into the holes in the stems 4 and 6 to prevent contact of the sensor faces when the device is in a closed position. Sensor ends in contact with the fluid may be provided with jewelled windows, as in the case of sensors using light, x-ray, or similar elements. Sensors which require direct contact with the fluid will not need this protection.

The stems are advanced and retracted to expose the light path 51 to the flowing fluid path 11. The depth of view is varied by adjustment of the separation distance between the stems 4 and 6. The sampling zone may be varied by moving both stems simultaneously by equal distances in the desired direction. When the stems are fully advanced, intimate contact of the stem 4 concave surface 7 and the stem 6 convex surface 8 isolates the sensor from the fluid flow path 11 and permits the removal, cleaning and reinstallation of the probes 1 and 5 while allowing fluid flow to continue uninterrupted. The device may be provided with a jacket means 15 for circulation of a heat transfer fluid if required to maintain the fluid in a molten or heated state, as in a polymer stream.

In the event that the stem surfaces 7 and 8 become fouled, a means is provided for cleaning these surfaces without the need for process stream shutdown. Slot 27 is machined so as to allow for an approximately 90 degree rotation of stem 4. Key 28 prevents further rotation. By advancing the stems until surfaces 7 and 8 are in contact, gripping stem 4 at flats 53 using a wrench or other means, and rotating both stem 4 and handle 17 back and forth at the same time, stem 4 is caused to rotate back and forth relative to stem 6 while maintaining contact of the stem surfaces 7 and 8, thus wiping the surfaces to clean them. The arrangement of stem 6 is identical to that of stem 4, allowing for rotation of either or both of stems for cleaning purposes.

Figure 4:
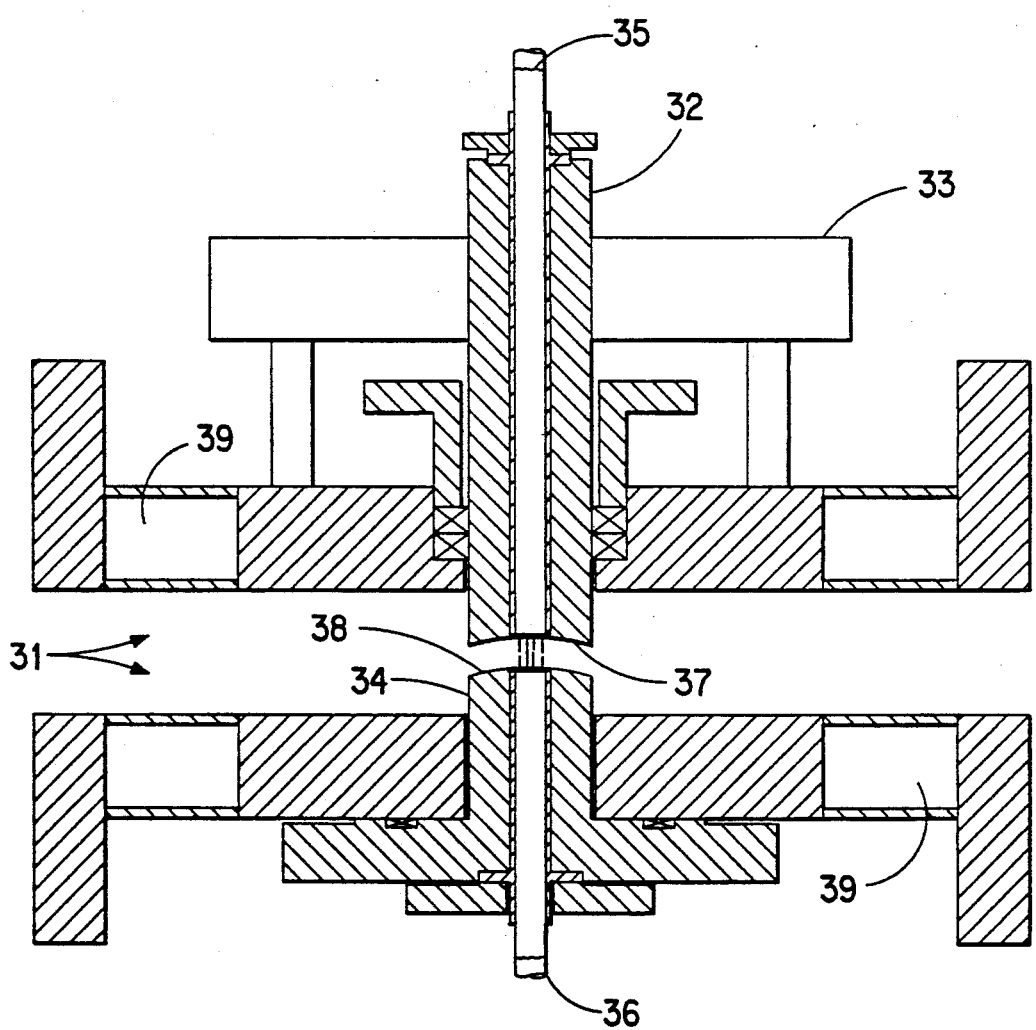
FIG. 4 is a cross-sectional side elevation view of an embodiment of the device in which one stem is stationary and one stem is retractable.

FIG. 4 illustrates another embodiment of the present invention in which the stem 32 is movable but in which the seat 34 is fixed. Operation is similar to the embodiment given in FIGS. 1-3. The stem 32 is advanced and retracted by means of stem operating mechanism 33 which may be identical to the rising stem mechanism illustrated in the embodiment of FIGS. 1-3. Stem 32 may also be designed to provide for rotation relative to stem 34 for cleaning purposes as shown in the embodiment of FIGS. 1-3. The depth of view may be adjusted by varying the position of the non-rotating stem 32 in the fluid path 31. When stem 32 is in its fully advanced position, intimate contact of the stem and seat surfaces 37 and 38 provides a leak-proof seal, thus allowing the removal, cleaning and reinstallation of the sensor probes 35 and 36. The device may also be provided with a jacket means 39 for circulation of heat transfer fluid if required.

The above description is provided by way of example only. The sensor end, holding device stem and seat openings, and windows may be redesigned depending on the requirements of a particular sensor device to provide a leak-tight fit. A variety of seat/stem complementary mating configurations, such as tapered, rounded, flat, convex/concave and concave/convex, are possible.

What is claimed is:

1. A sensing apparatus to determine characteristics of a fluid flowing in a stream by sensing said characteristics in various zones in the cross section of the stream, said apparatus comprising: a body member having an inlet end, an outlet end and a passage defining said stream connecting said inlet end to aid outlet end; a valve stem coupled to said body, aid valve stem being movable through aid stream to engage a seat located directly opposite said valve stem, said valve stem having a passage therethrough whereby said passage is sealed from said stream when said valve stem engages said set a; and a sensor closely fitted in the passage of said valve stem.

2. A sensing apparatus to determine characteristics f a fluid flowing a stream by sensing said characteristics in various zones in the cross section of the stream, said apparatus comprising: a body member having an inlet end, an outlet ned and a passage defining said stream connecting said inlet end to said outlet end; a valve steam coupling to said body and movable through said steam to engage a seat located directly opposite valve stem, said valve stem and said seat each having a passage therethrough whereby said passages are sealed from said stream said valve stem engages said set a; a signal source closely fitted in the passage of said valve steam; and a detector closely fitted in the passage o the seat.

3. A sensing apparatus to determine characteristics of a fluid flowing in a stream by sensing said characteristics in various zones in the cross section of the stream, said apparatus comprising: a body member having an inlet end, an outlet end and a passage defining said steam connecting said inlet end to said outlet end; a pair f elongated valve stems coupled to said body, said valve stems having directly opposed mating surfaces, each stem being independently movable through said stream to engage said opposed mating surfaces, each stem having a longitudinal passage therethrough whereby said longitudinal passages are sealed from said stream when said opposed mating surfaces are engaged; a signal source closely fitted in the passage of one of said valve stems near its mating surface; and a detector closely fitted in the passage of the other of said valve stems near its mating surface.

4. The sensing apparatus as defined in claims 1, 2 or 3, said valve stems being non-rotatable.

5. The sensing apparatus as defined in claims 1, 2 or 3, said valve stems being rotatable.

* * * * *